United States Patent [19]

Watanabe et al.

[11] Patent Number: 4,988,887

[45] Date of Patent: Jan. 29, 1991

[54] METHOD OF INSPECTING DIE FOR FORMING HONEYCOMB STRUCTURE

[75] Inventors: Mitsuaki Watanabe, Inazawa; Masayoshi Nakane, Nagoya, both of Japan

[73] Assignee: NGK Insulators, Ltd., Aichi, Japan

[21] Appl. No.: 486,921

[22] Filed: Mar. 1, 1990

[30] Foreign Application Priority Data

Mar. 1, 1989 [JP] Japan ................................. 1-49598

[51] Int. Cl.$^5$ ............................................. G01N 21/88
[52] U.S. Cl. .................................. 250/572; 356/237; 356/241
[58] Field of Search ............... 250/571, 572, 559, 561, 250/562; 356/237, 241, 445, 446

[56] References Cited

U.S. PATENT DOCUMENTS

| | | | |
|---|---|---|---|
| 4,145,714 | 3/1979 | MacDonald et al. | 356/241 |
| 4,560,273 | 12/1985 | Ando et al. | 356/241 |
| 4,806,774 | 2/1989 | Lin et al. | 250/572 |

FOREIGN PATENT DOCUMENTS 64-3068  1/1989  Japan .

Primary Examiner—Edward P. Westin
Attorney, Agent, or Firm—Parkhurst, Wendel & Rossi

[57] ABSTRACT

A method of inspecting a die having slits of narrow widths and a number of rear apertures communicating with the slits for forming honeycomb structures is able to inspect roughness distributions on inner surfaces of the rear apertures of the die. The method includes steps of irradiating diffused light beams onto an end face of the die on a side of the slits, detecting intensities of light beams arrived at an end face of the die on a side of the rear apertures by irregularly reflecting at inner surfaces of the rear apertures by the use of photosensitive device such as sensitized paper arranged at the end face of the die on the side of the rear apertures, and finally determining roughness distributions of the inner surfaces of the number of rear apertures with the aid of bright and dark portions on the photosensitive device.

5 Claims, 3 Drawing Sheets

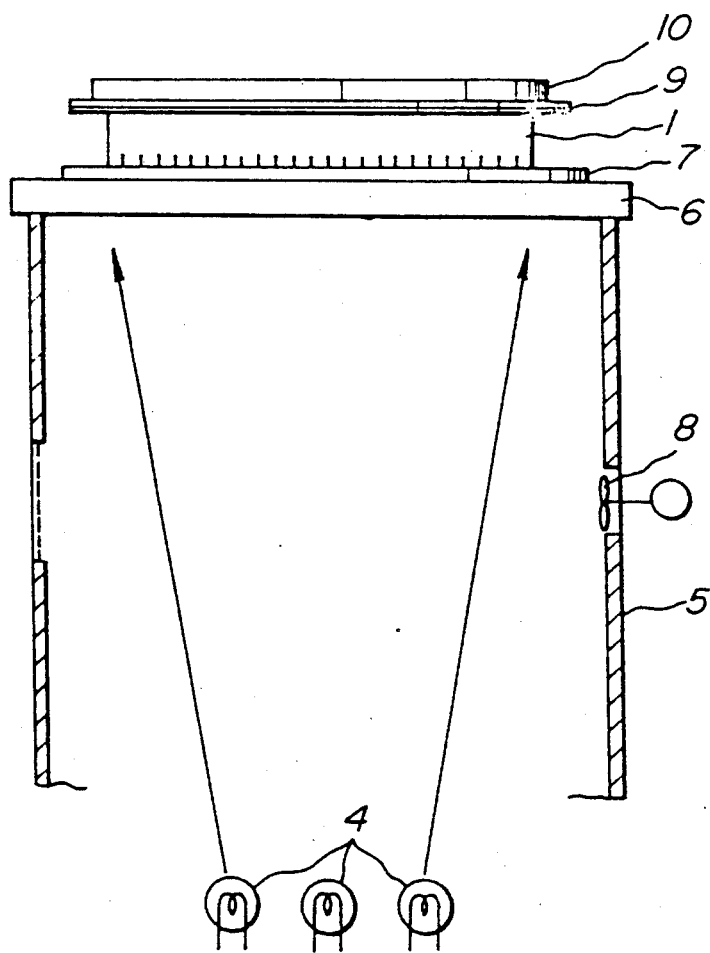
FIG_1

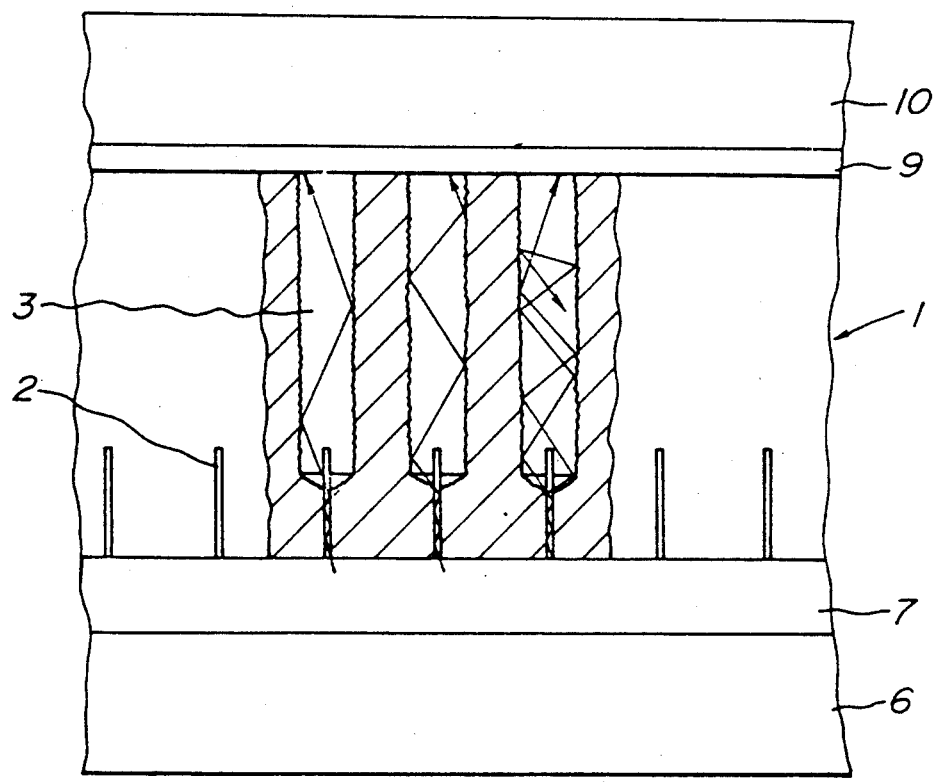
FIG_2

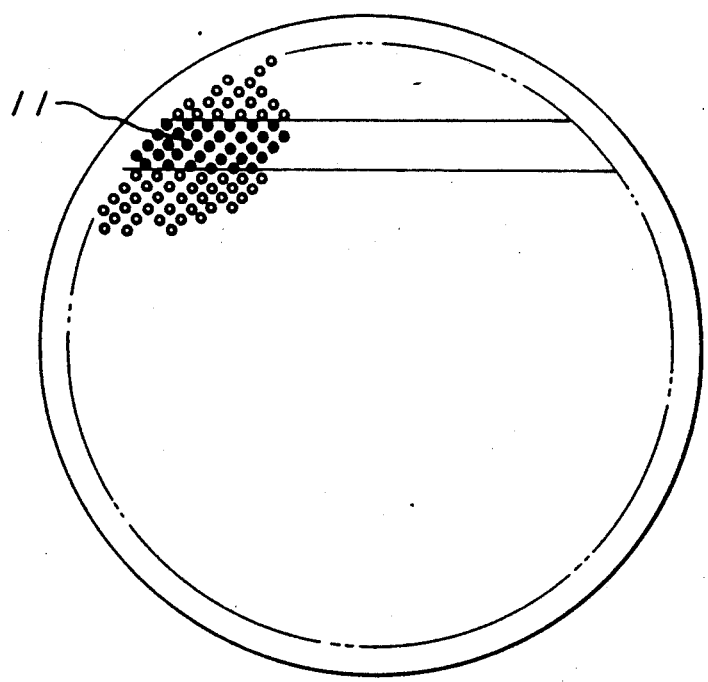
FIG_3

METHOD OF INSPECTING DIE FOR FORMING HONEYCOMB STRUCTURE

BACKGROUND OF THE INVENTION

This invention relates to a method of inspecting a die for forming honeycomb structures, and more particularly to a method of inspecting a die for forming honeycomb structures, which is able to precisely inspect worked conditions of inner surfaces in a great many rear apertures for supplying ceramic batches into the die.

Ceramic honeycomb structures have been widely used as catalyst carriers for purifying exhaust gases of automobiles. Such ceramic honeycomb structures are generally formed by extruding ceramic batches through a honeycomb forming die having slits of narrow widths of the order of 0.1–0.2 mm and a great number (as much as thousands) of rear apertures communicating with the slits for supplying the ceramic batches.

It is of course that quality of formed honeycomb structures is directly affected by configurations and dimensional accuracy of the slits of such honeycomb forming dies. In addition, since flowing resistance of ceramic batches passing through rear apertures of the die is affected by roughnesses of inner surfaces of the rear apertures for supplying the ceramic batches, it is needed to work the rear apertures so as to obtain uniform inner surface roughnesses in order to prevent malformed honeycomb structures. However, these rear apertures are great in number and very deep relative to their diameters so that a surface roughness tester cannot be used for measuring surface roughness on inner surfaces of the rear apertures. There has been no suitable inspecting method for this purpose. Therefore, when a new honeycomb forming die is used, it is unavoidable that the die is set in an extruding machine and honeycomb structures are actually formed whose defects are used for determining whether roughnesses of the rear apertures of the die fulfill the requirement or not. Such a judgment requires troublesome and time-consuming operations and gives rise to confusions in a production shop.

SUMMARY OF THE INVENTION

It is an object of the invention to provide a method of inspecting dies for forming honeycomb structures, which eliminates all the disadvantages of the prior art and is capable of simply and precisely inspecting roughness distributions, greatly affecting quality of honeycomb structures, of inner surfaces of rear apertures for supplying ceramic batches.

In order to accomplish this object, the method of inspecting a die having slits of narrow widths and a number of rear apertures communicating with the slits for forming honeycomb structures according to the invention, comprises steps of irradiating diffused light beams onto an end face of the die on a side of the slits, detecting intensities of light beams arrived at an end face of the die on a side of the rear apertures by irregularly reflecting at inner surfaces of the rear apertures by means of photosensitive means arranged at the end face of the die on the side of the rear apertures, and determining roughness distributions of the inner surfaces of the number of rear apertures with the aid of bright and dark portions on the photosensitive means.

The invention will be more fully understood by referring to the following detailed specification and claims taken in connection with the appended drawings.

BRIEF DESCRIPTION OF THE DRAWINGS

FIG. 1 is a sectional view for explaining the inspection method according to the invention;

FIG. 2 is an enlarged sectional view of a main parts shown in FIG. 1; and

FIG. 3 is a plan view illustrating images occurred on photosensitive means used in the invention.

DETAILED EXPLANATION OF THE PREFERRED EMBODIMENTS

FIGS. 1 and 2 illustrate a die 1 for forming honeycomb structures, which is to be inspected. The die 1 includes a number of slits 2 having very narrow widths and a number (as much as thousands) of rear apertures 3 communicating with the slits 2, respectively, for supplying ceramic batches. Such a die 1 is arranged through a support glass plate 6 and a light diffusion plate 7 such as a ground glass on an open upper surface of an inspection table 5 having light sources 4 therein. In this case, an end face of the die 1 on a side of the slits 2 is arranged facing to the light diffusion plate 7. It is further preferable to arrange the light sources 4 and the support glass plate 6 so that light beams from the light sources 4 have substantially equal intensities at a surface of the support glass plate 6 as shown in FIG. 2. It is further preferable to provide a fan 8 for cooling the inside of the inspection table 5.

On the other hand, photosensitive means 9 is provided on the other end face of the die 1 on a side of the rear apertures 3. The photosensitive means 9 is, for example, a sensitized paper which is brought into close contact with the end face of the die 1 by means of a weight 10. In this case, it is preferable to use light sources 4 radiating light beams of wave lengths to which the sensitized paper is most susceptible. As an alternative, means such as an image reader may be used as the photosensitive means 9, which is able to directly convert intensities of light into electric signals which are arithmetically processed to output inspection results onto a TV monitor.

With this arrangement, when light beams of the uniform intensity diffused through the light diffusion plate 6 are directed onto the end face of the die 1 on the side of the slits 2, the diffused light beams are irradiated uniformly into the number (as much as thousands) of the rear apertures 3 and irregularly reflected at inner surfaces of the rear apertures 3 to arrive at the end face of the die 1 on the side of the rear apertures 3. In this case, if roughnesses of the inner surfaces of the rear apertures 3 are fairly large, the degree of the irregular reflection becomes large. On the other hand, if the roughnesses of the inner surfaces of the rear apertures 3 are small, the degree of the irregular reflection becomes small. Therefore, the intensity of the diffused light beams arrived at the end face of the die 1 on the side of the rear apertures 3 through rear apertures having rougher inner surfaces is lower than that of the diffused light beams through rear apertures having smoother inner surfaces.

Such an intensity of the diffused light beams can be detected by the degree of bright and dark of light beams with the aid of the photosensitive means 9 such as a sensitized paper located on the end face of the die 1 on the side of the rear apertures 3. It is necessary to bring the photosensitive means 9 into close contact with the end face of the die 1 on the side of the rear apertures 3 in order to improve the inspection accuracy. If there is any clearance between the photosensitive means 9 and the end face of the die 1, clear bright and dark images cannot be obtained.

FIG. 3 illustrates examples of the images obtained on the photosensitive means 9. It is clear from the illustration that rear apertures 3 of the die 1 corresponding to partially dark portions 11 were worked badly or with rougher inner surfaces. The die 1 whose images were shown in FIG. 3 was actually set in an extruder to form honeycomb structures. As a result, it was ascertained that flowing resistance of ceramic batches through the apertures corresponding to the dark portions 11 was larger than those through remaining apertures. Therefore, the extrusion of the ceramic batch through the apertures corresponding to the dark portions was delayed so that structures (formed bodies) having uniform sections could not be obtained.

As can be seen from the above description, according to the invention diffused light beams having substantially equal intensities are irradiated from an end face of a die for forming honeycomb structures on a side of slits thereof and intensities of the light beams arrived at the other end face of the die on a side of rear apertures are detected in a simple manner by means of photosensitive means arranged on the other end face of the die. Accordingly, roughness distributions of inner surfaces of great number (as much as thousands) of the rear apertures of the die can be inspected easily and precisely only by one operation according to the invention. Therefore, according to the invention the quality of a die for forming honeycomb structures can be determined rapidly without trially forming honeycomb structures.

The method of inspecting dies for forming honeycomb structures according to the invention thus eliminates all the disadvantages of the prior art and contributes to great development of industries.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A method of inspecting a die having slits of narrow widths and a number of rear apertures communicating with the slits for forming honeycomb structures, said method comprising steps of irradiating diffused light beams onto an end face of the die on a side of the slits, detecting intensities of light beams arrived at an end face of the die on a side of the rear apertures by irregularly reflecting at inner surfaces of the rear apertures by means of photosensitive means arranged at the end face of the die on the side of the rear apertures, and determining roughness distributions of the inner surfaces of the number of rear apertures with the aid of bright and dark portions on the photosensitive means.

2. A method as set forth in claim 1, wherein a sensitized paper is used as said photosensitive means.

3. A method as set forth in claim 1, wherein an image reader is used as said photosensitive means.

4. A method as set forth in claim 1, wherein said diffused light beams have a wave length to which said photosensitive means is susceptible.

5. A method as set forth in claim 1, wherein said photosensitive means is in close contact with the end face of the die on the side of the rear apertures.

* * * * *